United States Patent [19]

Cross, Jr. et al.

[11] Patent Number: 4,603,696
[45] Date of Patent: Aug. 5, 1986

[54] LEAD CONNECTOR

[75] Inventors: Thomas E. Cross, Jr., St. Francis; Gerald J. Hults, Fridley, both of Minn.

[73] Assignee: Medtronic, Inc., Minneapolis, Minn.

[21] Appl. No.: 701,466

[22] Filed: Feb. 14, 1985

[51] Int. Cl.⁴ .............................................. A61N 1/36
[52] U.S. Cl. .................................. 128/419 P; 128/784
[58] Field of Search ............................ 128/419 P, 784

[56] References Cited

U.S. PATENT DOCUMENTS 4,236,525 12/1980 Sluetz et al. ...................... 128/419 P
4,437,474 3/1984 Peers-Trevarton .............. 128/419 P Primary Examiner—William E. Kamm
Attorney, Agent, or Firm—Reed A. Duthler; Joseph F. Breimayer; John L. Rooney

[57] ABSTRACT

A connection system for joining a medical electrical stimulator to its electrical stimulus delivery system features a first member having a row of more than two contact surfaces each spaced apart a given distance from the adjacent contact surfaces, and a second member having at least the same number of contacts in a row each spaced from the adjacent contact surface by a multiple of the spacing between the contact surfaces of the first member and each being connected to one of two electrical conductors so that electrical connections between the contact surfaces are varied as the two connector members are relatively moved along the rows.

6 Claims, 3 Drawing Figures

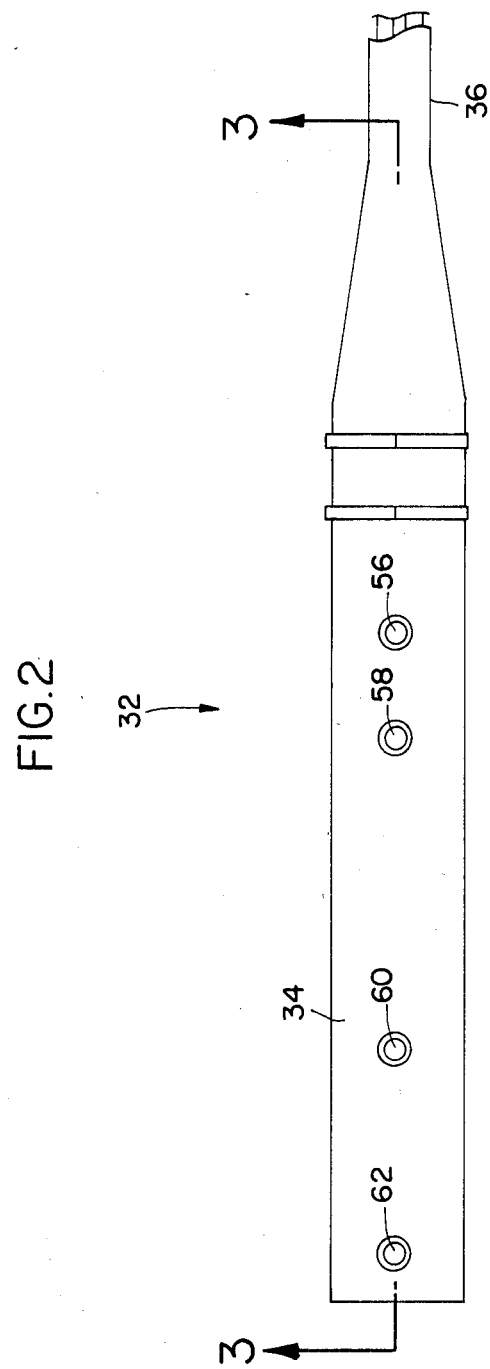

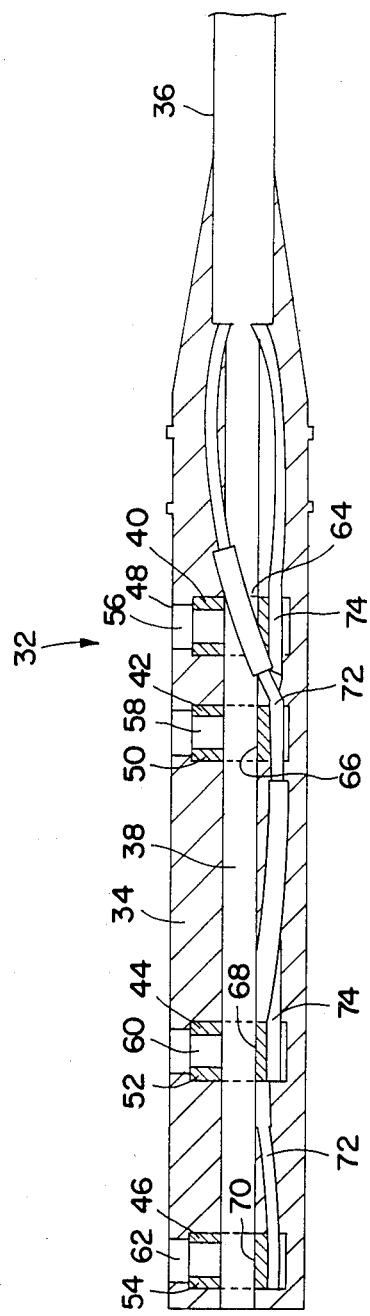

LEAD CONNECTOR

BACKGROUND OF THE INVENTION

1. Field of the Invention

This invention relates to connectors for medical electrode-bearing leads.

2. Prior Art

It is well known that more efficacious electrical stimulation of certain portions of the body may be obtained by using multiple electrode leads. Various combinations of electrodes may then be used for stimulating different portions of the body.

One example of this type of stimulation involves a four-electrode lead which is inserted in the epidural space adjoining the spinal column. In the past, spinal leads were inserted in place and then stimulated transcutaneously until the proper location was found. Once a lead was implanted, there was no possibility of changing the location of stimulation. With a multielectrode lead, the location can be altered. One type of lead used in such assemblies is the Medtronic ® PISCES-QUAD ® epidural lead which employs four cylindrical barrel electrodes spaced along the lead.

A female connector for pacemaker leads is illustrated in U.S. Pat. No. 4,236,525 to Sluetz et al, issued Dec. 2, 1980, in which the polarity of the two distal electrodes is reversed by repositioning the lead within the female connector assembly. In this design, both contacts in the female portion are always both used. The system allows for selecting two of the three contacts on the male lead to reverse polarity of two stimulating electrodes.

While this allows altering of polarity, it does not allow choice of electrodes through a programming system. What is needed is means to combine multiple electrodes in the available combinations and permutations. A connector is needed to connect four-electrode leads with two-conductor stimulators.

SUMMARY OF THE INVENTION

The present invention is a means for programming the selection of electrodes on a lead by use of a multi-contact connector. In one form of the invention, the connector includes a bore therethrough with multiple contacts arranged along a longitudinal axis in the bore. A lead having multiple lead contacts is positioned axially within the bore to determine which lead contacts electrically connect with certain connector contacts.

For example, this system allows a four-electrode lead to be connected in any combination of two electrodes with a two-conductor stimulation generator. In this example, one set of contacts is equidistantly spaced. The other set of contacts is staggered so that it is spaced in increments of the equidistance space. Positioning then puts two of the equidistantly spaced contacts in contact with two of the differently spaced contacts.

This invention allows combinations of electrodes to be selected. The polarity selection taught by Sluetz may be incorporated so that all permutations may be selected.

In the example illustrated, at least three connector contacts are positioned along the bore. Two of the contacts are spaced apart a distance equal to the spacing between lead contacts. Two contacts are spaced apart at distance equal to twice the distance between lead contacts. By choosing differing pairs, different lead contacts are selected, which, in turn, are electrically connected to different electrodes on the stimulating portion of the lead.

BRIEF DESCRIPTION OF THE DRAWINGS

FIG. 2 is a fragmentary top view of a connector constructed according to the present invention having four connector contacts; and FIG. 3 is a cross sectional view taken on line 3—3 of FIG. 2.

DETAILED DESCRIPTION OF THE DRAWINGS

Figure 1:
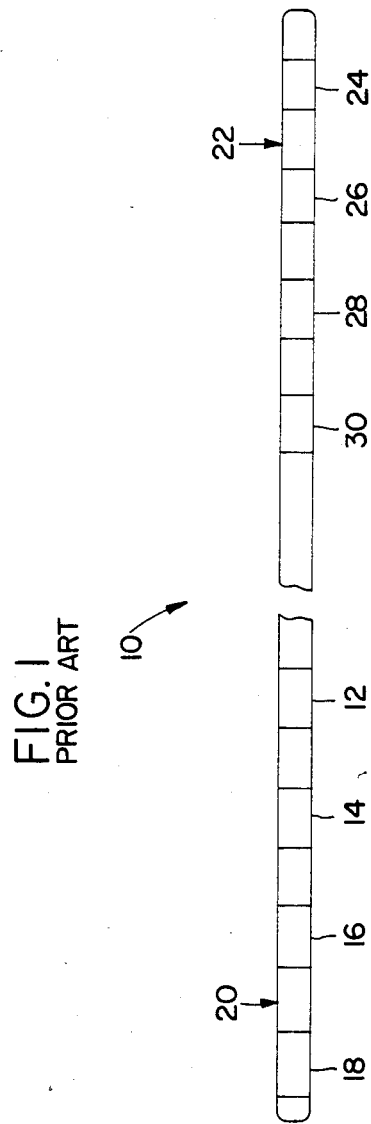
FIG. 1 is a fragmentary side elevational view of a lead having four axially spaced electrodes and four axially spaced lead contacts.

In FIG. 1, an illustrative prior art lead 10 includes barrel electrodes 12, 14, 16 and 18 on distal portion 20. Electrodes 12-18 are mounted in a conventional manner on lead 10 as is well known in the prior art. The electrodes 12-16 are generally spaced in equal increments successively away from the most distal electrode 18. Each electrode 12-18 is connected to its individual conductor (not shown) within lead 10 in a conventional manner.

Lead 10 includes a proximal portion 22 on which are mounted lead contacts 24, 26, 28 and 30. In the example illustrated, each contact 24-30 is individually connected by a separately insulated conductor (not shown) to one of electrodes 12-18. Therefore, selection of one contact 24-30 selects the corresponding electrode 12-18.

When placed in the epidural space, any two of electrodes 12-18 may be selected for stimulation. For stimulating different portions, for example, any of the pairs 16 and 18, 14 and 16, or 12 and 14 could be selected. Also, a larger area of stimulation can be selected. Electrodes 14 and 18, 12 and 16, or even 12 and 18 could be selected. In various embodiments, polarity may be reversed.

Connector 32 is designed to receive proximal portion 22 of lead 10. Connector 32 includes a connector body 34 made of biocompatible material, such as molded silicone rubber in this embodiment. Connector body 34 is attached to lead extension 36, which is, in turn, connected to a source of electrical stimulation (not shown).

Connector body 34 is provided with a central lead-receiving bore 38 sized to snugly receive proximal portion 22 of lead 10. In this embodiment, bore 38 is cylindrical for the receipt of typical prior art lead 10.

Mounted within connector body 34 are connectors 40, 42, 44, and 46. Connectors 40-46 are adjacent to openings 48, 50, 52 and 54, which extend through connector body 34 from bore 38 to the external surface of connector body 34. Mounted through each opening 48-54 into connectors 40-46, are set screws 56, 58, 60 and 62, respectively.

Connectors 40-46 are made of 304 stainless steel in this embodiment. Connectors 40-46 include connector contacts 64, 66, 68, and 70, respectively, which form cylindrical paths for receiving lead contacts 24-30 in electrical contact. Contacts 64-70 are in individual electrical contact with separately insulated conductors. In this embodiment, contacts 66 and 70 are both connected to conductor 72. Contacts 64 and 68 are both connected to conductor 74. Of course, in other embodiments, each contact has an individual conductor.

When one lead contact 24-30 is positioned within one connector 40-46, electrical contact is made between it and contact 64-70 of connectors 40-46. Electrical contact is also made by set screw 56-62 which is in electrical contact with conductor 72 or 74 through connector 40-46. When electrical contact is described herein with contacts 64-70 or connectors 40-46, it includes contact with set screws 56-62.

Contacts 64-70 are positioned along bore 38 of connector 32 in positions, the distance between which are multiples of the distance between each pair of contacts 24-30. In this embodiment, the distance between connector contacts 64 and 66 is generally equal to that between any two of lead contacts 24-30. The distance between connector contacts 68 and 70 is generally equal to two times the distance between contacts 64 and 66. The distance between contacts 66 and 68 is approximately three times the distance between contacts 64 and 66.

Therefore, connector 32 includes means to select combinations of contacts 24-30 of lead 10. The location of a lead 10 within connector 32 in this embodiment determines the contact 24-30 selection and, therefore, determines which two, and only two, of lead contacts 24-30 comes in contact with two of connector contacts 64-70.

For example, to select contacts 24 and 26, proximal portion 22 of lead 10 is inserted in bore 38 of connector 32 until contact 24 is in electrical contact with contact 64. Because of the equal spacing, contact 26 is in electrical contact with contact 66. Contacts 28 and 30 remain unconnected in the area between contacts 66 and 68.

To select contacts 24 and 28, proximal portion 22 of lead 10 is inserted in bore 38 of connector 32 until connector 24 is in electrical contact with contact 68. Contact 26 then lies between contacts 68 and 70 and remains out of electrical contact. Contact 28 is in electrical contact with contact 70.

To connect contacts 24 and 30, lead 10 is inserted until contact 24 is in electrical contact with connector 66. Contact 30 is then in electrical contact with contact 68. Contacts 26 and 28 remain unused in the area between contacts 66 and 68.

To connect contacts 26 and 28, lead 10 is inserted until contact 26 is in electrical contact with contact 64. Contact 28 is then in electrical contact with contact 66. Contacts 24 and 30 remain out of contact on either side of the pair of contacts 64 and 66.

To connect electrodes 26 and 30, lead 10 is inserted in connector 32 until contact 26 is in electrical contact with contact 68. This positions contact 30 in electrical contact with contact 70. Contact 24 is out of contact in the area between contacts 66 and 68. Contact 28 is out of contact in the area between contacts 68 and 70.

Similarly, to connect contacts 28 and 30, lead 10 is inserted in connector 32 until contact 28 electrically contacts contact 64. Contact 30 then contacts the contact 66. Contacts 24 and 26 are past contact 64 and out of electrical connection.

Once proximal portion 22 of lead 10 is properly positioned within bore 38 of connector 32, the appropriate set screws 56-62 are tightened down upon contacts 24-30 to hold lead 10 fixedly within connector 32.

One skilled in the art may arrange other numbers and combinations of electrodes and contacts through this programming scheme. With this apparatus, multiple electrode leads may be connected to leads or pulse generators having a different number of electrodes. For example, a four pole lead may have two poles selected for connection to an implantable pulse generator. Similarly, polarity may be changed in the manner taught by Sluetz. While the invention has been disclosed in terms of a four electrode embodiment, one skilled in the art may determine many other embodiments with which to practice this invention.

What is claimed:

1. A connector system for connecting a medical electrical lead to a medical electrical stimulator, comprising:

a first connector member having a first predetermined number of electrical connector surfaces, mutually insulated from one another, mounted linearly along said first connector member such that each of said predetermined number of contact surfaces is spaced a first predetermined distance from the contact surfaces immediately adjacent thereto and such that said first predetermined number of connector surfaces extends over a second predetermined distance on said first connector member and wherein said first predetermined number is greater than two; and second connector member means for slideably engaging said first connector member, said second connector member means including a second predetermined number of electrical contact surface means, arranged linearly along said second connector member means, for contacting selected ones of said first predetermined number of electrical contact surfaces on said first connector member when said first connector member is slideably engaged with said second connector means, said second predetermined number being at least equal to said first predetermined number, said second connector member means further comprising first and second conductors, wherein each of said second predetermined number of connector surface means is coupled to only one of said first and second conductors and such that each of said second predetermined number of connector surface means is coupled to a different one of said first and second conductors from the connector surface means immediately adjacent to it, said second predetermined number of electrical connector surfaces spaced from one another such that each connector surface means is spaced a multiple of said first predetermined distance from each adjacent connector surface means and such that each connector surface means is spaced a distance greater than said second predetermined distance from any other connector surface means coupled to the same one of said first and second conductors.

2. A connector system according to claim 1 wherein said first connector member is located on the proximal end of said medical electrical lead and wherein said second electrical connector is coupled to said medical electrical stimulator.

3. A connector system according to claim 1 or claim 2 wherein said second connector member means comprises a longitudinal bore along which said second predetermined number of connector surface means are arranged and wherein said first connector member is insertable in said bore of said second connector means.

4. A connector assembly for coupling a medical electrical lead to a medical electrical stimulator, comprising:

a first connector member having a first predetermined number of connector surfaces, mutually insulated from one another, arranged linearly along said first connector member, said first predetermined number being greater than two; and second connector.member means for slideably engaging said first connector member, and comprising a second predetermined number of electrical contact surface means for contacting selected ones of said first predetermined number of contact surfaces on said first connector member when said first connector member means is slideably engaged with said second connector member means, said second connector means including first and second conductor means, wherein each of said second predetermined number of connector surface means is electrically coupled to only one of said first and second conductors, said second predetermined number of electrical contact surface means arranged linearly along said second connector member means such that while said first connector member is slideably engaged with said second connector means, any two of said first predetermined number of connector surfaces on said first connector member may be coupled to different ones of said first and second electrical conductors.

5. A connector system according to claim 4 wherein said first connector member is located on the proximal end of said medical electrical lead and wherein said second electrical connector is coupled to said medical electrical stimulator.

6. A connector system according to claim 4 or claim 5 wherein said second connector member means comprises a longitudinal bore along which said second predetermined number of connector surface means are arranged and wherein said first connector member is insertable in said bore of said second connector means.

* * * * *